US00PP37772P2

(12) United States Plant Patent

Macgregor et al.

(10) Patent No.: US PP37,772 P2
(45) Date of Patent: Oct. 13, 2026

(54) *GEUM* PLANT NAMED 'MACGEU051'

(50) Latin Name: ***Geum* hybrid**
Varietal Denomination: MACGEU051

(71) Applicants: Elizabeth Macgregor, Kirkcudbright (GB); Alasdair John Macgregor, Kirkcudbright (GB)

(72) Inventors: Elizabeth Macgregor, Kirkcudbright (GB); Alasdair John Macgregor, Kirkcudbright (GB)

(73) Assignee: Elizabeth MacGregor's Nursery, Kirkcudbright (GB)

( * ) Notice: Subject to any disclaimer, the term of this patent is extended or adjusted under 35 U.S.C. 154(b) by 0 days.

(21) Appl. No.: 19/632,203

(22) Filed: Mar. 28, 2026

(51) Int. Cl.
*A01H 5/02* (2018.01)
*A01H 6/74* (2018.01)

(52) U.S. Cl.
USPC ..... Plt./263.1

(58) Field of Classification Search
USPC ..... Plt./263.1
See application file for complete search history.

(56) References Cited

U.S. PATENT DOCUMENTS

PP28,476 P2 * 10/2017 MacGregor ..... A01H 6/74
Plt./263.1

* cited by examiner

*Primary Examiner* — Susan Mccormick Ewoldt
(74) *Attorney, Agent, or Firm* — James R. Holm; Plant Novelty Rights, LLC

(57) ABSTRACT

A new and distinct *Geum* plant named 'MACGEU051' particularly distinguished by semi-double flowers, which are approximately 20 percent larger than all *Geum* cultivars known to the inventors, unique soft, orange-colored flowers with a subtle orange-red shading which provides a distinctive warm-toned appearance, and a long bloom period from April to September in the Netherlands.

4 Drawing Sheets

Figure 1:
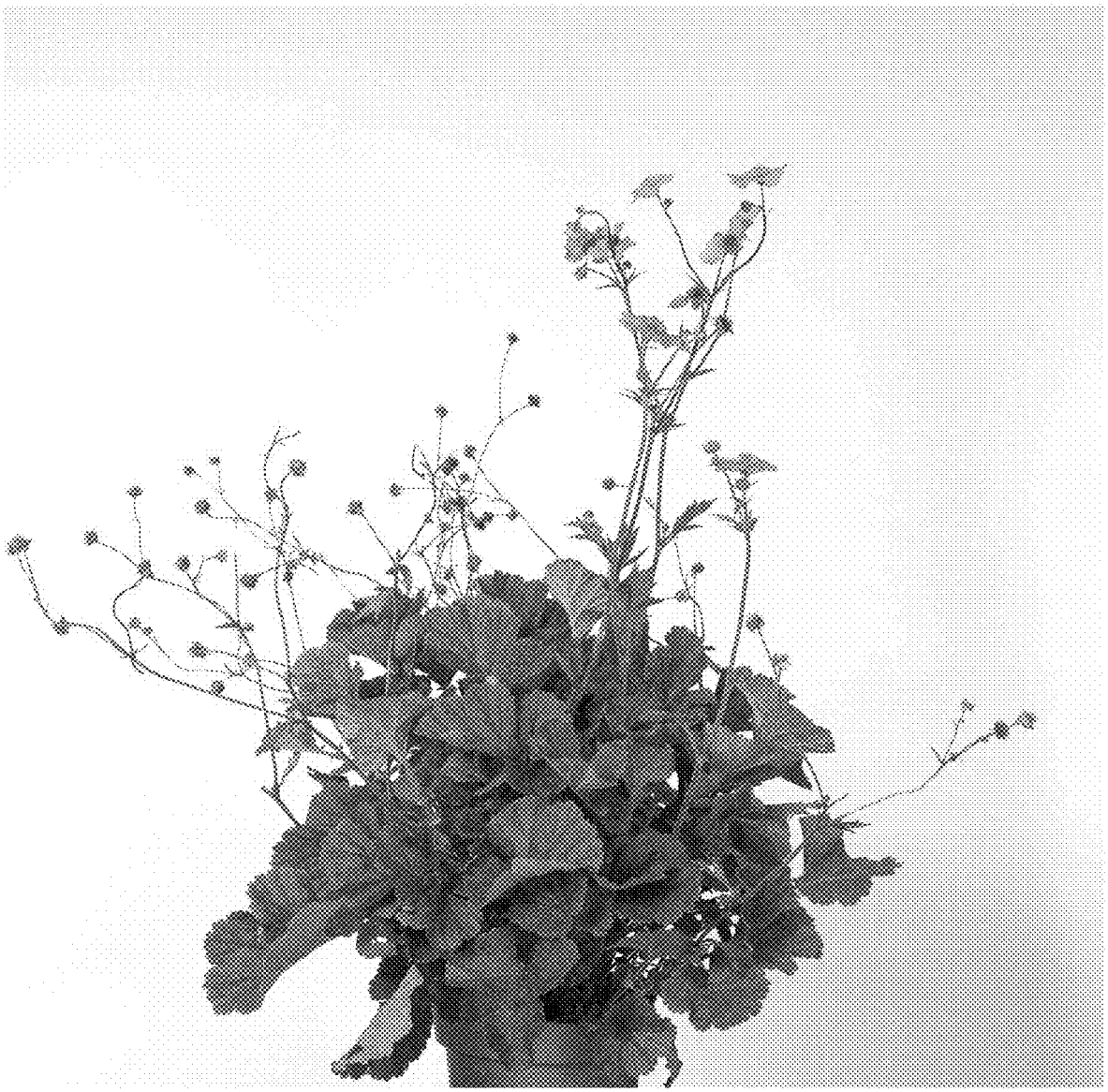

Genus and species: *Geum* hybrid.
Variety denomination: 'MACGEU051'.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period prior to the filing date.

BACKGROUND OF THE NEW PLANT

The present invention comprises a new and distinct variety of *Geum* plant, botanically known as *Geum* hybrid, and hereinafter referred to by the variety name 'MACGEU051'. The new *Geum* variety 'MACGEU051' is the result of a controlled cross-pollination breeding program carried out by the inventors in a commercial nursery located in Kirkcudbright, Scotland in 2018. The inventors performed the controlled cross-pollination between *Geum* 'Beech House Apricot' (unpatented), as the seed parent, with an unnamed and unpatented *Geum* F1 hybrid (*Geum* 'Lady Stratheden' x *Geum* hybrid no. 10), as the pollen parent. Said pollination was carried out in an insect proof environment. Seed from said cross was harvested, then germinated, and the resulting seedlings were grown to a mature size in a protected poly tunnel house from January 2019 to July 2019. In July 2019, the inventors selected the new *Geum* cultivar for its novel flower and bloom characteristics including flower size, longevity of flowers and unique soft orange flower color. This new and distinctive *Geum* cultivar was given the name 'MACGEU051'.

The new *Geum* cultivar 'MACGEU051' was first reproduced asexually in 2020 by meristematic tissue culture at a laboratory in Heerhugowaard, the Netherlands. Asexual propagation by meristematic tissue culture has shown that the unique features of the new cultivar are stable and reproduced true-to-type to date through five successive generations.

SUMMARY OF THE INVENTION

The new *Geum* cultivar 'MACGEU051' has not been observed under all possible environmental conditions. The phenotype may vary somewhat with variations in environment such as temperature, day length, light intensity, water status, fertilizer rate and type, without, however, any variance in genotype.

The following are the most outstanding and distinguishing characteristics of this new cultivar. The combination of these characteristics distinguishes 'MACGEU051' as a new and distinct variety of *Geum*.

1. *Geum* 'MACGEU051' exhibits large, semi-double flowers, which are approximately 20 percent larger than all *Geum* cultivars known to the inventors.
2. *Geum* 'MACGEU051' exhibits unique soft, orange-colored flowers with a subtle orange-red shading which provides a distinctive warm-toned appearance.

3. *Geum* 'MACGEU051' exhibits a long bloom period from April to September in the Netherlands.

DESCRIPTION OF THE PHOTOGRAPHS

This new *Geum* cultivar is illustrated by the accompanying-colored photographs which show the overall appearance and distinct characteristics of the plant. The colors shown are as true as can be reasonably obtained by conventional photographic procedures. The photographs are of 3-month-old plants grown in 19-centimeter circular containers in an outdoor nursery in Kirkcudbright, Scotland. Colors in the photographs may differ slightly from the color values cited in the botanical description which accurately describes the colors of the new variety.

FIG. 1. shows the overall plant form, foliage, and inflorescence of 'MACGEU051'.

Figure 2:
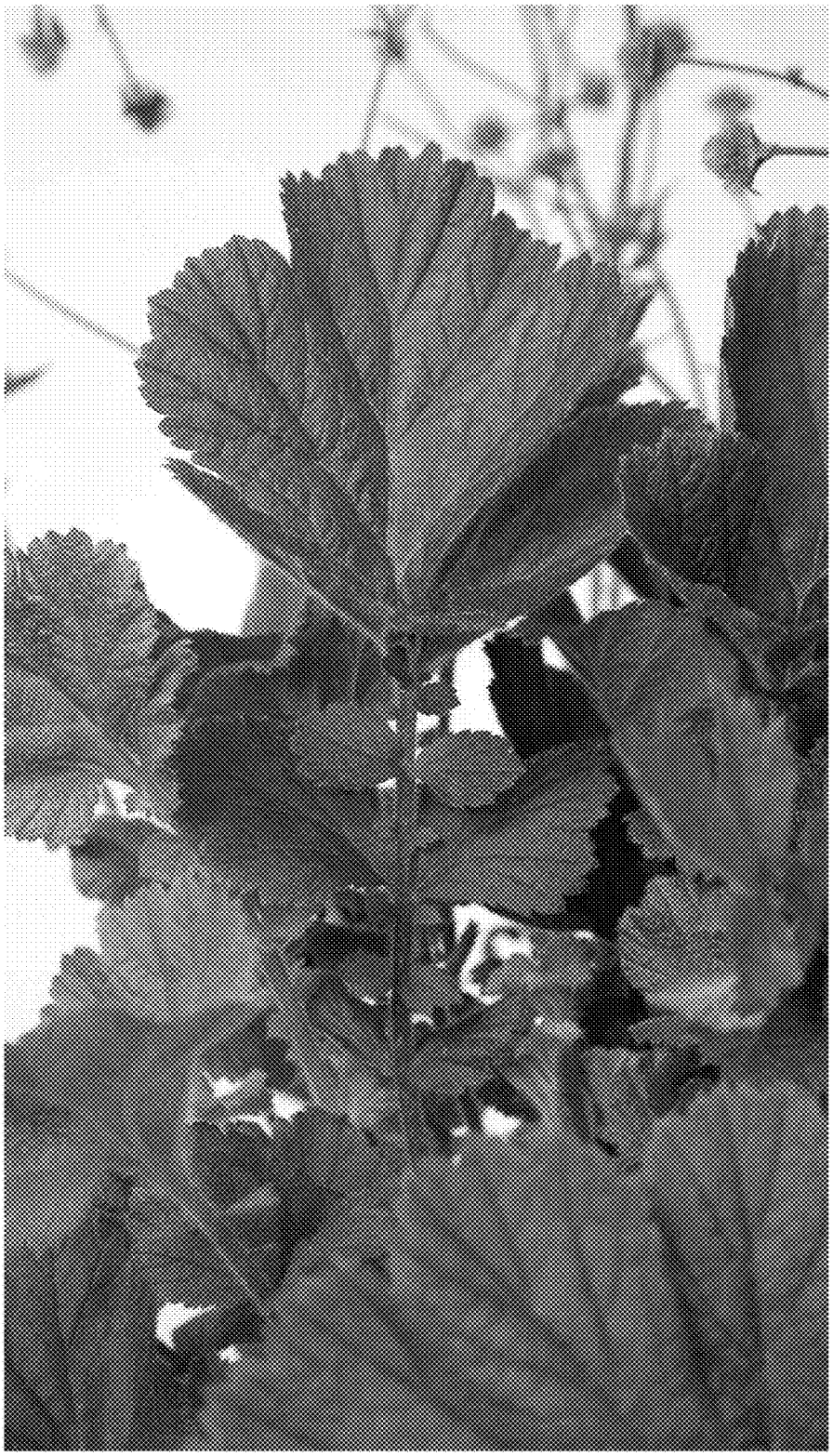

FIG. 2. shows a close-up of typical foliage of 'MACGEU051'.

Figure 3:
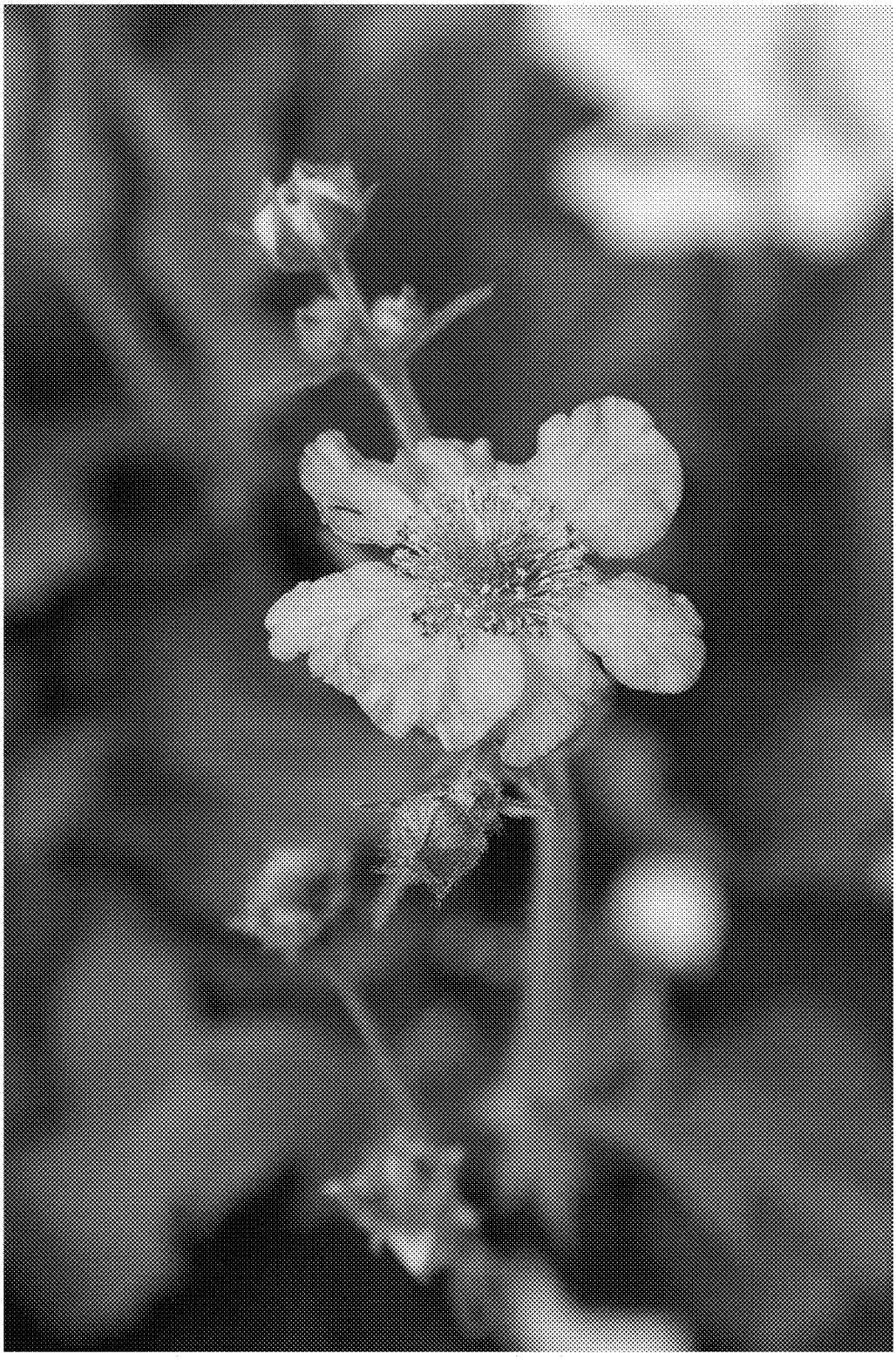
Figure 4:
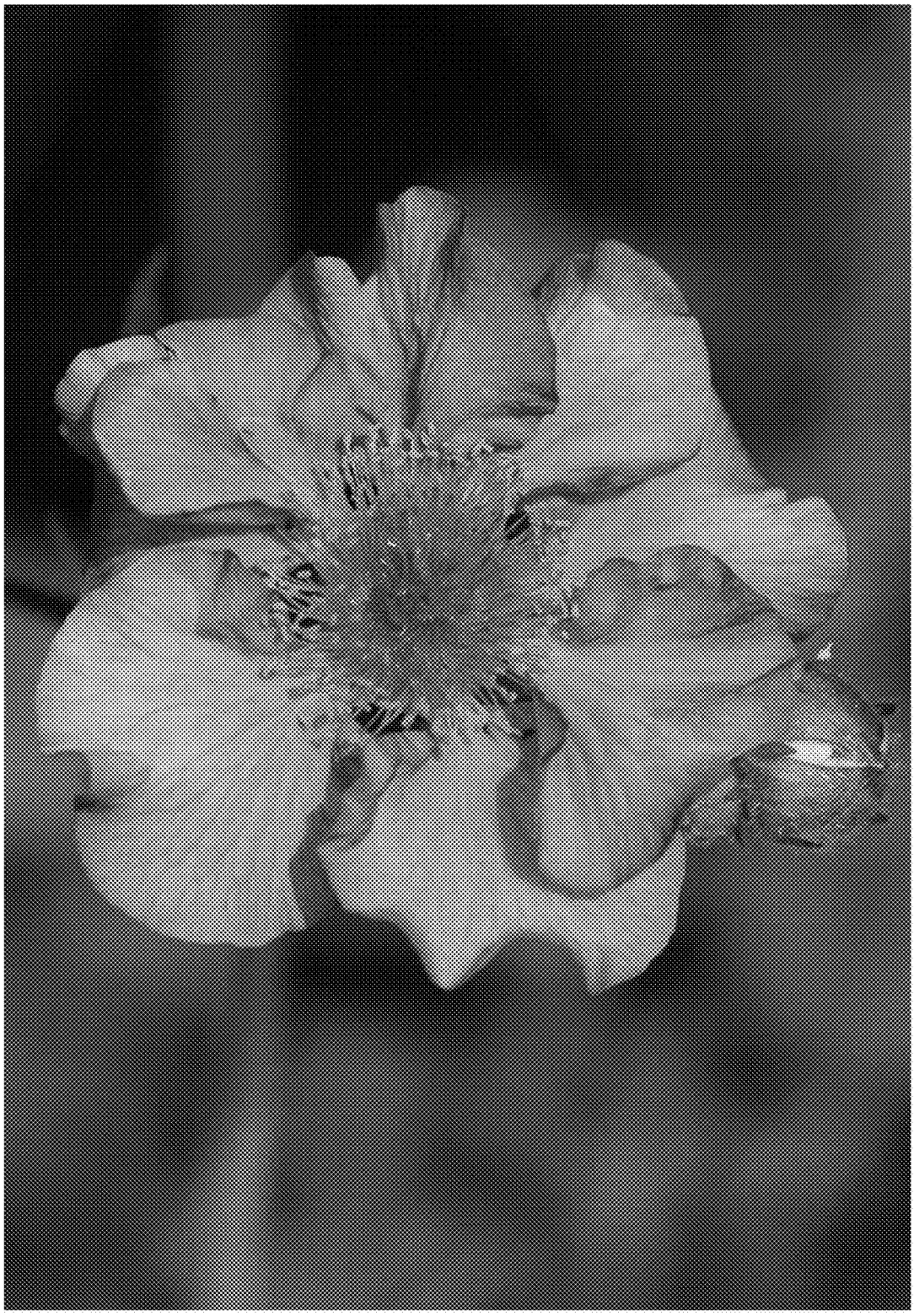

FIG. 3. and FIG. 4. show close-ups of typical flowers of 'MACGEU051'.

DESCRIPTION OF THE NEW VARIETY

In the following description, color references are made to The Royal Horticultural Society Colour Chart, Sixth Edition, except where general color terms of ordinary dictionary significance are used.

The following observations and measurements describe plants grown in an outdoor nursery located in Kirkcudbright, Scotland. Detailed descriptions were taken in July 2025 from 3-month-old plants grown in 19-centimeter circular containers. Measurements and numerical values represent averages of typical plant types.

DETAILED BOTANICAL DESCRIPTION

Classification:

*Family*.—Rosaceae.

*Botanical*.—*Geum* hybrid.

*Denomination*.—'MACGEU051'.

General description:

*Growth habit*.—A broad, irregular and inverted triangular shaped herbaceous perennial with flowering stems arising from the base with no lateral branching.

*Height from soil level to top of foliar plane*.—Average 35.1 cm.

*Height from soil level to top of floral plane*.—Average 75.3 cm.

*Plant diameter or area of spread*.—Average 84.3 cm.

*Plant vigor*.—High.

*Growth rate*.—Moderate to high.

*Time to produce a flowering plant from a rooted cutting*.—Approximately 26 weeks; no pinching required.

*Propagation type*.—Meristematic tissue culture.

Stems:

*Branching habit*.—Basally branched; freely branching.

*Number of primary (main) stems per plant*.—13.

*Number of secondary (lateral) branches per plant*.—None.

*Appearance and shape*.—Rounded.

*Length*.—Average 43.1 cm from the base of the plant to the lowest branching inflorescence.

*Diameter*.—Average 0.4 cm.

*Internode length*.—Average 10.8 cm.

*Luster*.—Slightly glossy.

*Attitude*.—Average angle of 30 degrees from vertical; stems vary between 0 to 60 degrees from vertical.

*Strength*.—Strong.

*Color*.—Juvenile stems: 146A and 146B (yellow-green) and tinged 165A (greyed-orange). Mature stems: 144A (yellow-green) and tinged 148A (yellow-green). At internodes: 144A (yellow-green) and tinged 148A (yellow-green).

*Pubescence*.—Densely covered with soft hairs having an average length of 0.15 cm and colored 156D (greyed-white).

Foliage description:

*General*.—Leaves are borne both basally and on stems.

*Arrangement*.—Alternate.

*Basal leaves*.—Attachment: Petiolate. Division: Imparipinnate; average of 19 leaflets (varying between 17 and 23 per basal leaf). Shape: Whole leaf: Narrow obovate in outline. Lateral leaflets: Broad ovate. Terminal leaflet: Reniform and lobed. Whole leaf dimensions: Length (including petiole and rachis): Average 35.9 cm. Width: Average 12.1 cm. Lateral leaflet dimensions: Length: Average 2.7 cm (varying between 0.3 cm and 4.7. cm). Width: Average 2.2 cm (varying between 0.2 cm and 4.3 cm). Terminal leaflet dimensions: Length: Average 11.5 cm. Width: Average 12.1 cm. Lobes (terminal leaflet only): Quantity of lobes: 3 and occasionally 5. Depth of sinus: Shallow to medium. Sinus orientation: Divergent. Aspect: Moderately carinate. Apex shape: Short and abruptly acute. Base shape: Lateral leaflets: Broad attenuate. Terminal leaflet: Truncate to cordate. Margin: Serrate. Texture (adaxial and abaxial surfaces): Smooth. Pubescence (adaxial and abaxial surfaces): Densely covered with soft strigose hairs having an average length of 1.5 mm and colored 156D (greyed-white). Rugosity: Non-rugose. Luster: Adaxial surface: Slightly glossy. Abaxial surface: Matte. Color: Juvenile foliage: Adaxial surface: 143B (green). Abaxial surface: 138B (green). Mature foliage: Adaxial surface: 137B (green). Abaxial surface: 146B (green). Venation: Type: Pinnate. Color: Adaxial surface: 143A (green). Abaxial surface: 145A (yellow-green). Petiole (including rachis): Length: Average 26.4 cm. Shape and diameter: Flattened; average of 0.4 cm on the widest surface and average of 0.35 cm on the narrowest surface. Strength: Medium to high. Color (adaxial and abaxial surfaces): 144A (yellow-green). Pubescence: Densely covered with soft hairs having an average length of 1.5 mm and colored 156D (greyed-white). Luster: Slightly glossy. Stipules: None present.

*Leaves borne on stems*.—Quantity: Approximately 5 leaves per stem. Attachment: Petiolate. Division: Simple. Shape: Obovate to broad elliptic in outline. Lobes: Quantity of lobes: 3. Depth of sinus: Deeply cleft to near parted. Sinus orientation: Divergent. Aspect: Moderately carinate. Length (including petiole): Average 5.3 cm. Width: Average 3.9 cm. Apex shape: Acute to narrow acute. Base shape: Attenuate. Margin: Serrate. Texture (adaxial and abaxial surfaces): Smooth. Pubescence (adaxial and abaxial surfaces): Densely covered with soft strigose hairs having an average length of 1.5 mm and colored 156D (greyed-white). Rugosity: Non-rugose. Luster: Adaxial surface: Slightly glossy. Abaxial surface: Matte Color: Juvenile foliage: Adaxial surface: 137C (green). Abaxial surface: 137D (green). Mature foliage: Adaxial surface: 137B (green). Abaxial surface: 146B (green). Venation: Type: Pinnate. Color: Adaxial surface: 143A (green). Abaxial surface: 151B (yellow-green). Petiole: Length: Average 2.6 cm. Diameter: Average 0.2 cm. Color: Adaxial surface: A blend of 144A and 144B (yellow-green). Abaxial surface: 144B (yellow-green). Pubescence: Densely covered with soft hairs having an average length of 1.5 mm and colored 156D (greyed-white). Luster: Slightly glossy. Stipules: General: Two leafy stipules present at the base of each stem leaf. Shape: Ovate to obovate. Length: Average 2.1 cm. Diameter: Average 1.2 cm. Margin: Serrate. Apex: Narrow acute. Base: Narrow cuneate. Color: Adaxial surface: 137B (green). Abaxial surface: 146B (green). Pubescence (adaxial and abaxial surfaces): Densely covered with soft hairs having an average length of 1.5 mm and colored 156D (greyed-white).

Inflorescence description:

*Type*.—Cyme.

*Natural flowering season*.—April to September.

*Time to flower or response time*.—9 months.

*Height*.—Average 39.2 cm.

*Width*.—Average 23.6 cm.

*Quantity of inflorescence per plant*.—Average 11.

*Quantity of flowers per plant*.—Average 20.

*Quantity of flower buds per plant*.—Average 130.

*Quantity of flowers and flower buds per plant*.—150.

*Peduncles*.—Length: Average 23.4 cm. Diameter: Average 0.3 cm. Orientation: Upright. Strength: Strong. Pubescence: Densely covered with soft hairs having an average length of 0.15 cm and colored 156D (greyed-white). Luster: Slightly glossy. Color: 144A (yellow-green) and tinged slightly darker, nearest to 152A (yellow-green).

*Pedicels*.—Length: Average 4.6 cm. Diameter: 0.2 cm. Angle to peduncle axis: Main flowers: Average 0 degrees. Secondary flowers: Average 30 degrees. Strength: Moderate. Texture: Smooth. Pubescence: Densely covered with soft hairs having an average length of 0.1 cm and colored 156D (greyed-white). Luster: Slightly glossy. Color: 146B (yellow-green) with the upper, sun-facing side colored 177A (greyed-orange).

Flower buds:

*Shape*.—Broad ovate to near deltoid.

*Length*.—Average 0.9 cm.

*Diameter*.—Average 0.9 cm.

*Texture*.—Smooth.

*Pubescence*.—Densely covered with soft hairs having an average length of 0.1 cm and colored close to 156D (greyed-white), but too minute to accurately describe color designation.

*Luster*.—Matte.

*Color*.—145A (yellow-green) and 174B (greyed-orange) towards the apex; veined darker, nearest to 177A and 177B (greyed-orange).

Flower:

*Shape and type*.—Rotate; semi-double.

*Habit*.—Freely.

*Orientation*.—Upright to outwardly.

*Longevity*.—Approximately 10 days.

*Persistent or self-cleaning*.—Self-cleaning.

*Fragrance*.—Non-fragrant.

*Height and diameter*.—Average 5.0 cm.

*Depth*.—Average 1.7 cm.

*Calyx*.—Shape: Rotate. Length: Average 1.1 cm. Diameter: Average 1.2 cm. Sepals: Arrangement: One whorl of sepals alternating between broad sepals and narrow sepals; broad sepals strongly reflexed, narrow sepals moderately reflexed. Quantity: 10 unfused sepals; 5 broad sepals and 5 narrow sepals. Texture (upper and lower surfaces): Smooth. Pubescence (upper and lower surfaces): Sparsely to moderately covered with soft hairs having an average length of 0.1 cm and shorter; colored close to greyed-white, but too minute to accurately describe color designation. Luster (upper and lowers surfaces) Matte. Broad sepals: Shape: Narrow deltoid. Length: 1.0 cm. Width: 0.6 cm. Apex: Long apiculate. Base: Truncate. Margin: Entire. Color (when opening): Upper surface: 145A (yellow-green). Lower surface: 146B (yellow-green) and tinged darker, nearest to 152B (yellow-green). Color (when fully opened): Upper surface: 145A (yellow-green). Lower surface: 146B (yellow-green). Narrow sepals: Shape: Narrow elliptic. Length: 0.5 cm. Width: 0.15 cm. Apex: Narrow acute. Base: Attenuate. Margin: Entire. Color (when opening and when fully opened): Upper surface: 146B (yellow-green). Lower surface: 145A (yellow-green).

*Petals*.—Quantity: 6, occasionally 7. Arrangement: Rotate in a single, non-fused whorl. Length: 1.9 cm. Width: 2.3 cm. Shape: Reniform. Apex: Shallow emarginate to near obtuse. Base: Broad acuminate. Margin: Entire and highly undulated; sparsely covered with soft strigose hairs having an average length of 0.1 cm and colored 156D (greyed-white). Texture (upper and lower surfaces): Glabrous, smooth and slightly velvety. Rugosity: Non-rugose. Luster (upper and lower surfaces): Matte. Color (when opening): Upper surface: 23A (yellow-orange). Lower surface: 20A (yellow-orange). Color (when fully opened): Upper surface: 24A (orange) and N25A (orange) towards the apex and margins. Lower surface: 22B (yellow-orange) and 25C (orange) towards the apex and margins. Color (when fading): Non-fading. Venation color (when fully opened): Upper surface: 24A (orange). Lower surface: 31A and 31B (orange).

Reproductive organs:

*Stamens*.—Quantity per flower: Average 150. Anthers: Shape: Oblong and dorsifixed. Length: Average 0.1 cm. Width: Average 0.5 mm. Color: 13A (yellow). Filaments: Length: Average 0.5 cm. Color: 12A (yellow). Pollen: Amount: Low. Color: 20A (yellow-orange).

*Pistil*.—Quantity per flower: Average 75. Length: Average 0.5 cm. Style: Length: Average 0.47 cm. Color: 153D (yellow-green). Stigma: Shape: Pointed. Length: Average 0.3 mm. Diameter: Average 0.5 mm. Color: 34B (orange-red). Ovary color: 143B (green).

Seed and fruit: Non observed to date.

USDA hardiness zones: 10 to 13.

Hight temperature tolerance: At least tolerant to temperatures up to 35 degrees Celsius.

Low temperature tolerance: At least tolerant to temperatures down to minus 25 degrees Celsius.

Rain tolerance: Low to moderate.

Wind tolerance: Moderate to high.

Disease and pest tolerance: No claims are made to any superior disease or insect resistance or tolerance.

COMPARISON WITH THE SEED PARENT

The new *Geum* cultivar 'MACGEU051' can be distinguished from its seed parent *Geum* 'Beach House Apricot' (unpatented) in the following characteristics described in Table 1 below.

TABLE 1

| Characteristic | 'MACGEU051' | 'Beach House Apricot' |
|---|---|---|
| Flower color. | Bright orange with red-orange shading toward petal margins, creating a more contrasting appearance. | Soft apricot to peach orange, more pastel and uniform appearance. |
| Flower center color. | Distinct yellow to orange contrasting strongly with the petal color. | Darker, often more reddish-brown. |
| Petal shape and margin. | Reniform with strong margin undulation and slightly irregular outline. | Flatter, more rounded and with less pronounced undulation. |
| Flower size. | Larger. | Slightly smaller. |
| Inflorescence density. | Flowers more loosely arranged along stems. | Flowers more numerous and more densely arranged. |
| Plant habit. | Broad, open and more spreading habit. | More compact, rounded, and bushier habit. |
| Flowering stems. | Longer, more slender and arching stems. | Shorter, more upright and compact stems. |

COMPARISON WITH RELATED KNOWN VARIETY

The new *Geum* cultivar 'MACGEU051' can be distinguished from the related known variety of *Geum* 'MACGEU001' (U.S. Plant Pat. No. 28,476) in the following characteristics described in Table 2 below.

TABLE 2

| Characteristic | 'MACGEU051' | 'MACGEU001' |
|---|---|---|
| Flower color. | Bright orange with distinct red-orange shading toward the petal margins, creating a bicolored effect. | More uniform orange to orange-red, lacking the bicolored effect. |
| Petal shape and margin. | Reniform with strong margin undulation and slightly irregular outline. | Flatter, more uniform and less margin undulation. |
| Flower appearance. | | |
| Inflorescence density. | Flowers more loosely arranged along stems. | Flowers more densely clustered. |
| Plant habit. | Broad, open and more spreading habit. | More compact and upright. |
| Flowering stems. | Longer, more slender and arching stems. | Shorter, sturdier and more upright. |
| Plant vigor and spread. | More vigorous with a wider spread and less dense canopy. | More compact. |

What is claimed is:

1. A new and distinct cultivar of *Geum* plant named 'MACGEU051', substantially as illustrated and described herein.

* * * * *